United States Patent [19]

Kato et al.

[11] 4,053,579
[45] Oct. 11, 1977

[54] METHOD FOR MANUFACTURE OF SINTERED ALUMINA FROM AMMONIUM ALUMINUM CARBONATE HYDROXIDE

[75] Inventors: Shuzo Kato; Takeo Iga, both of Nagoya; Shogo Hatano, Minami-Minowa; Yuichi Isawa, Takato, all of Japan

[73] Assignee: Agency of Industrial Science & Technology, Tokyo, Japan

[21] Appl. No.: 623,489

[22] Filed: Oct. 17, 1975

[30] Foreign Application Priority Data

May 29, 1975 Japan .................................. 50-65076

[51] Int. Cl.² .......................... C01F 7/02; C01C 1/26; A61K 33/10

[52] U.S. Cl. .................. 423/630; 423/419 P; 423/625; 423/631; 423/427; 424/154; 424/156

[58] Field of Search ............... 423/114, 115, 127, 128, 423/419, 420, 421, 625, 628, 629, 631, 156, 158; 424/154, 156

[56] References Cited

U.S. PATENT DOCUMENTS

| | | | |
|---|---|---|---|
| 2,783,124 | 2/1957 | Grote | 423/420 |
| 2,783,127 | 2/1957 | Grote | 423/428 |
| 3,264,124 | 8/1966 | Lauder et al. | 423/631 |
| 3,557,025 | 1/1971 | Emerson | 423/419 |
| 3,714,343 | 1/1973 | Sato et al. | 423/628 |
| 3,911,090 | 10/1975 | Hem et al. | 423/419 |

*Primary Examiner*—O. R. Vertiz
*Assistant Examiner*—Gary P. Straub
*Attorney, Agent, or Firm*—Oblon, Fisher, Spivak, McClelland & Maier

[57] ABSTRACT

Aluminum carbonate hydroxide ammonium, a new compound, is produced by causing a solution of ammonium hydrogencarbonate to be reacted upon by a soluble aluminum salt. α-Alumina is obtained by thermal decomposition of this ammonium aluminum carbonate hydroxide. By sintering said α-alumina, there is obtained sintered α-alumina.

2 Claims, 9 Drawing Figures

METHOD FOR MANUFACTURE OF SINTERED ALUMINA FROM AMMONIUM ALUMINUM CARBONATE HYDROXIDE

BACKGROUND OF THE INVENTION

This invention relates to ammonium aluminum carbonate hydroxide (hereinafter referred to as $NH_4AlCO_3(OH)_2$), to a method for the manufacture thereof and to a method for the manufacture of sintered α-alumina from said $NH_4AlCO_3(OH)_2$.

Concerning aluminum compounds of this kind, there have heretofore been known to the art naturally produced dawsonite (a mineral having the composition $NaAlCO_3(OH)_2$) and synthetically produced $NaAlCO_3(OH)_2$ and $KAlCO_3(OH)_2$. A few reports have been published covering conditions for the formation of these aluminum products and the properties thereof.

These substances are synthesized by blowing carbon dioxide gas into a solution of sodium aluminate and a solution of potassium aluminate. In the solution of alkali aluminate which has had the alkali moiety thereof neutralized and has consequently become supersaturated with aluminate ions, $NaAlCO_3(OH)_2$ or $KAlCO_3(OH)_2$ is produced when a large amount of $HCO_3^-$ is brought into existence therein. For this condition to be satisfied, it is necessary to increase the molar ratio of $Na_2O/Al_2O_3$ or $K_2O/Al_2O_3$ in said alkali aluminate solution and blow carbon dioxide gas rapidly into the solution. The properties of the product are variable with the conditions under which the production is performed. The production on a commercial scale, therefore, requires fairly complex control of operational conditions.

The $NaAlCO_3(OH)_2$ and $KAlCO_3(OH)_2$ thus produced enjoy excellent filterability and combine decolorizing, deodorizing, deacidifying and heat-insulating functions and, therefore, and finding increasingly more industrial applications.

Moreover, these aluminum compounds exhibit unique properties in their powdery form and are used as the raw materials for the production of α-alumina, a substance for which there have been found numerous uses. Said aluminum compounds, however, comprise a large amount of involatile alkali components such as Na or K so that in the production of α-alumina, for example, a preparatory treatment for the removal of such alkali components is necessary. This required treatment limits their uses.

Sintered alumina possesses excellent physical, chemical and thermal properties and, for this reason, is used extensively in various industrial fields. It has heretofore been customary to obtain a compact product of sintered alumina by roasting at elevated temperatures the aluminum hydroxide produced by the Bayer process and thereby converting it into α-alumina, pulverizing the α-alumina for a long time, thereafter adding to the pulverized α-alumina an agent for inhibiting growth of crystals and an agent for accelerating sintering or molding such as, for example, magnesium oxide or clay and finally firing the resultant mixture at high temperatures in the neighborhood of 1900° C where there is desired a high-purity sintered alumina having not less thand 99% of alumina content or at temperatures around 1550° C where there is desired a low-purity sintered alumina having about 85% af alumina content.

This method, however, has the following disadvantages: Since the α-alumina produced by the Bayer process consists of coarse grains, it entails the disadvantage of necessitating a long time of pulverization. At the same time, during the prolonged pulverization, the substance rubbed off of the wall of the pulverizing machine mingles into the particles under treatment and consequently degrades the purity of the pulverized alumina. Even if the pulverization is carried out amply, it is difficult both technically and economically to effect to size reduction beyond a certain level as, for example, to the extend of increasing the proportion of particles measuring not more than 1 μm to at least 50%. Thus, the pulverized particles have a small specific surface area and exhibit a poor sintering property, involving a drawback that the sintering must be carried out at higher temperatures.

An object of the present invention is to provide ammonium aluminum carbonate hydroxide, a new compound which possesses commercially more desirable properties and permits production of α-alumina more easily than the conventional aluminum carbonate hydroxide compounds.

Another object of the present invention is to provide a method for the manufacture of ammonium aluminum carbonate hydroxide which is a new compound.

Still another object of the present invention is to provide a method for manufacturing a compact sintered alumina at notably low temperatures.

BRIEF SUMMARY OF THE INVENTION

To accomplish the objects described above, the present invention causes ammonium aluminum carbonate hydroxide (hereinafter referred to as $NH_4AlCO_3(OH)_2$) to be manufactured by gradually adding to a solution of ammonium hydrogencarbonate a solution of a soluble aluminum salt (with the exception of Na or K salt) in an amount of not more than 0.75 equivalent weight and not less than 0.075 equivalent weight, mixing the two solutions, subsequently allowing the mixed solution to age for a prescribed period of time to permit growth of crystals therein, then separating the precipitate therefrom by filtration and drying the filtered precipitate.

The $NH_4AlCO_3(OH)_2$ manufactured by this method is a new compound which has not existed in the past. It is a white powdery solid. This $NH_4AlCO_3(OH)_2$, when heated, is decomposed to give rise to α-alumina. This α-alumina exhibits a better sintering property than the conventional α-alumina generally obtained by the Bayer process. To be specific, it produces sintered alumina of a compact texture when it is heated at a temperature about 200 Centigrade degrees lower than that at which the α-alumina is produced by the Bayer process.

Figure 1:
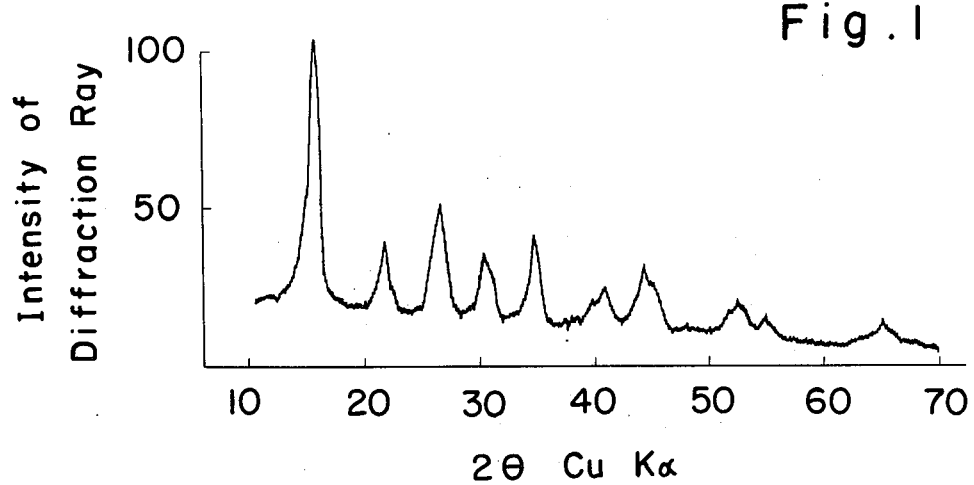
FIG. 1 is an X-ray diffraction diagram of $NH_4AlCO_3(OH)_2$.

DETAILED DESCRIPTION OF THE INVENTION:

First a description will be made of the method of the present invention for the manufacture of $NH_4AlCO_3(OH)_2$. The inventors conducted various studies with a view to developing an aluminum compound which is obtained in the form of a powdery product of high purity convenient for industrial applications and, therefore, can be put to a rich variety of uses. They have consequently acquired a new knowledge that $NH_4AlCO_3(OH)_2$, a new aluminum compound of the structure having $NH_4$, a volatile radical, substituted for the Na or K moiety in the known compound of $NaAlCO_3(OH)_2$ or $KAlCO_3(OH)_2$, is produced by gradually adding to a solution of ammonium hydrogencarbonate to a solution of a soluble aluminum salt (with the exception of Na or K salt) in an amount of not more than 0.75 equivalent weight and not less than 0.075 equivalent weight and thereby allowing the compounds to react with each other.

Thus, the present invention concerns a method which is based on a chemical reaction heretofore unknown to the art.

The reaction of an ammonium hydrogencarbonate salt with an aluminum salt which constitutes itself the basic component of the reaction of this invention will be explained with reference to specific examples. When a solution of aluminum chloride and a solution of ammonium aluminum sulfate are used each as the soluble ammonium salt, reactions are inferred to proceed as indicated below.

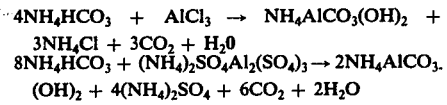

To be more specific, a white precipitate excelling in sedimenting property is obtained by gradually adding to a solution of ammonium hydrogencarbonate prepared in advance (by blowing carbonate carbon dioxide gas into aqua ammonia, for example) a solution of a soluble aluminum salt such as aluminum chloride, aluminum nitrate, aluminum sulfate or ammonium aluminum sulfate (with the exception of Na or K salt) in an amount of not more than 0.75 equivalent weight and not less than 0.075 equivalent weight and thereby allowing the compounds to react with each other. A soft finely divided product is obtained by allowing the resultant reaction mixture to age under continued agitation for 15 minutes following the termination of said reaction, washing the aged mixture by means of decantation, separating the precipitate therefrom by filtration, dehydrating the separated precipitate and finally drying the dehydrated precipitate.

There are several factors governing the smoothness with which the formation of $NH_4AlCO_3(OH)_2$ is obtained by the method of the present invention. They include the kind of the particular aluminum salt used as the raw material, the concentration of said salt, the rate of the addition of said salt, the reaction temperature, the pH value of the reaction system and the chemical equivalent ratio of said aluminum salt to the ammonium hydrogencarbonate salt ($AL/NH_4$).

These factors will be described specifically hereinafter.

The aluminum salts and basic salts thereof which are advantageous for the present invention include aluminum chloride, aluminum nitrate, aluminum sulfate and ammonium aluminum sulfate. This is because these slats are readily available commercially and mostly in a highly purified form. Of those salts enumerated above, ammonium aluminum sulfate proves to be particularly advantageous.

In the solution of ammonium hydrogencarbonate, the concentration of this ammonium salt is required to fall in the range of from 40 to 270 g/liter. In the case of the solution of a soluble aluminum salt, the concentration of said aluminum salt is required to be in the range of from 5 to 150 g/liter computed as aluminum oxide. The reason for these ranges is that, when the concentrations of said solutions exceed their respective ranges, the reaction system undergoes gelation and the product consequently obtained defies easy washing the therefore fails to acquire high purity.

For this reaction to proceed smoothly, the temperature is required to fall in the range of from 25° to 65° C. If the reaction temperature is lower than this range, the reaction entails formation of boehmite and the product shows a degraded sintering property. If the reaction temperature is higher than the range, then the decomposition of ammonium hydrogencarbonate is accelerated so much that the reaction fails to proceed effectively at the prescribed rate of dropwise introduction and the product sufferes from excessive growth of crystals and consequently entails a decline in sintering property. Preferably, the reaction temperature should fall in the range of from 30° to 45° C.

Furthermore, for the reaction to proceed effectively, it is necessary that the soluble aluminum salt solution be added gradually to the ammonium hydrogencarbonate solution. The rate at which said aluminum salt or basic salt thereof is added is required to exceed 0.5 cc and not to exceed 30 cc per minute per 1,000 cc of the ammonium hydrogencarbonate solution. If the rate is higher than this range, the pH status of the reaction system is rendered unstable and the growth of crystals is impeded, making it difficult to obtain $NH_4AlCO_3(OH)_2$ of high purity. The product, therefore, cannot be filtered and washed sufficiently as desired. If it is lower than the range, since ammonium hydrogencarbonate graudually decomposes itself at temperatures above 30 ° C, there ensue declined pH value and insufficient supply of $HCO_3^-$ ions. The pH value of the reaction solution must be maintained in the range of from 7.5 to 9.0.

The aluminum compound of the present invention obtained as described above is a powdery product which excels in filtering, washing, dehydrating and drying property and, therefore, can readily be refined. This compound, when heated, undergoes decomposition at temperatures around 223° C to produce a γ-$Al_2O_3$ of high activity with liberation of $NH_3$ and $CO_2$ and, as the temperature further rises to the neighborhood of 1,200° C, readily undergoes α-rearrangement to produce an α-Al₂O₃ of high purity. This compound of the present invention is a novel one.

FIG. 1 is an X-ray diffraction diagram of the compound of this invention (obtained by the procedure dealt with in Example 2). In the diagram, the horizontal axis is graduated for diffractive angle $2\theta$ and the vertical axis is graduated for intensity of diffraction ray. Table 1 indicates the results of FIG. 1 numerically in comparison with the data obtained for the conventional compounds $NaAlO(OH)HCO_3$ and $KAlO(OH)HCO_3$.

(Table 1)

x-ray analysis of synthetic MAlO(OH)HCO₃ (M: Alkali)

| NaAlO(OH)HCO₃ | | KAlO(OH)HCO₃ | | New Compound | |
|---|---|---|---|---|---|
| d(Å) | I/I₀ | d(Å) | I/I₀ | d(Å) | I/I₀ |
| 5.7 | 100 | 5.574 | 100 | 5.867 | 100 |
| — | — | 4.114 | 45 | 4.114 | 18 |
| 3.385 | 70 | 3.363 | 78 | 3.339 | 47 |
| — | — | 3.153 | 95 | — | — |
| 2.82 | 90 | 2.823 | 50 | 2.931 | 20 |
| 2.607 | 65 | 2.644 | 25 | 2.585 | 27 |
| 2.504 | 50 | 2.522 | 85 | 2.534 | 5 |
| 2.23 | 40 | 2.161 | 37 | 2.204 | 8 |
| 2.156 | 55 | — | — | 2.045 | 28 |
| 1.993 | 75 | 1.989 | 70 | 2.002 | 5 |
| 1.95 | 45 | — | — | — | — |
| 1.732 | 65 | — | — | 1.737 | 20 |
| 1.692 | 63 | 1.675 | 20 | 1.664 | 5 |
| 1.622 | 63 | 1.631 | 15 | — | — |

Figure 2:
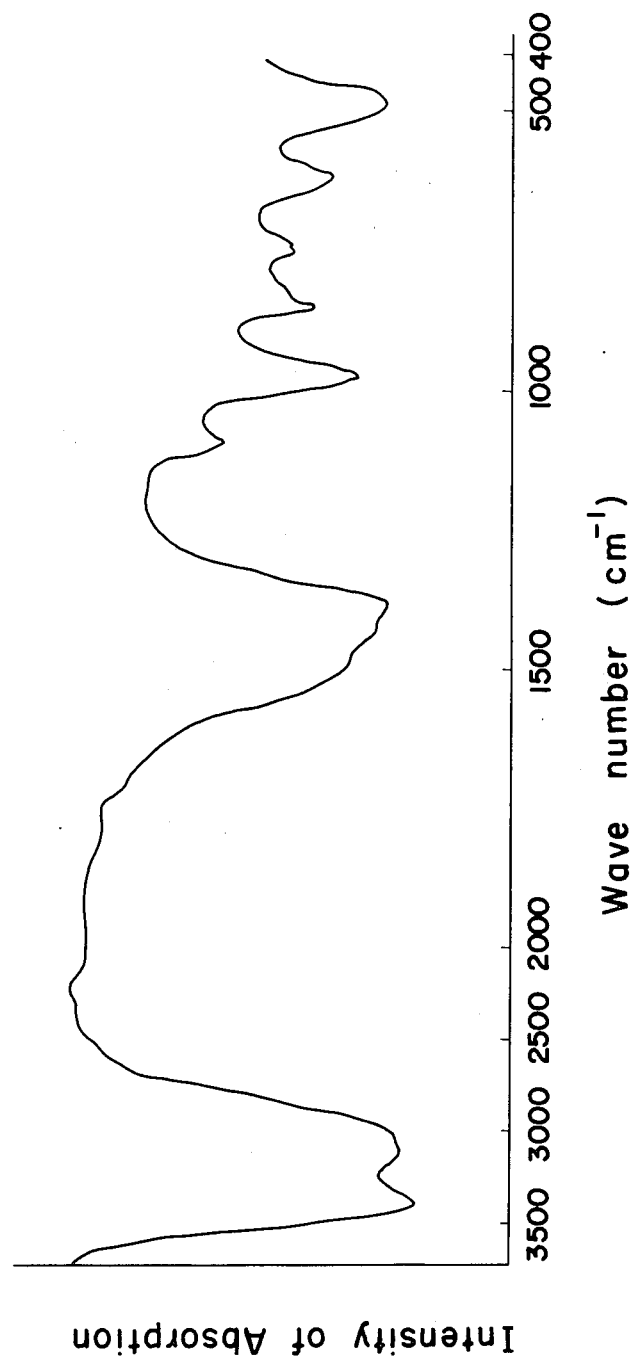
Fig. 2 is an infrared absorption spectrum $NH_4AlCO_3(OH)_2$.
Figure 4:
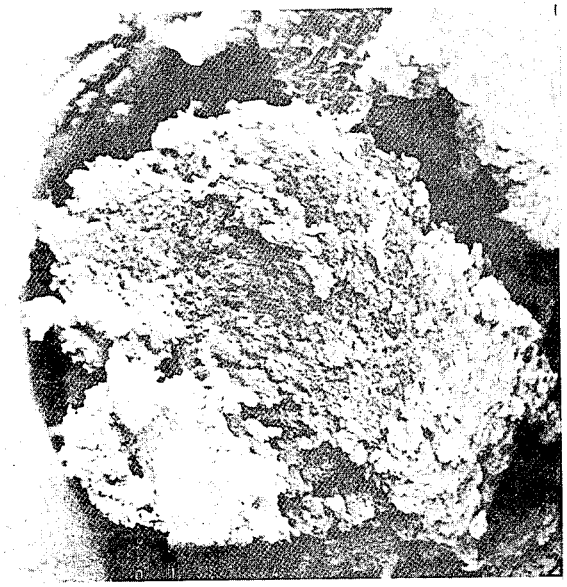
FIG. 4 is a scanning electron microscope photograph of a 1 × 10[4] magnification of $NH_4AlCO_3(OH)_2$ produced by reacting ammonium hydrogencarbonate with 0.3 equivalent weight of aluminum salt at 25° C.
Figure 5:
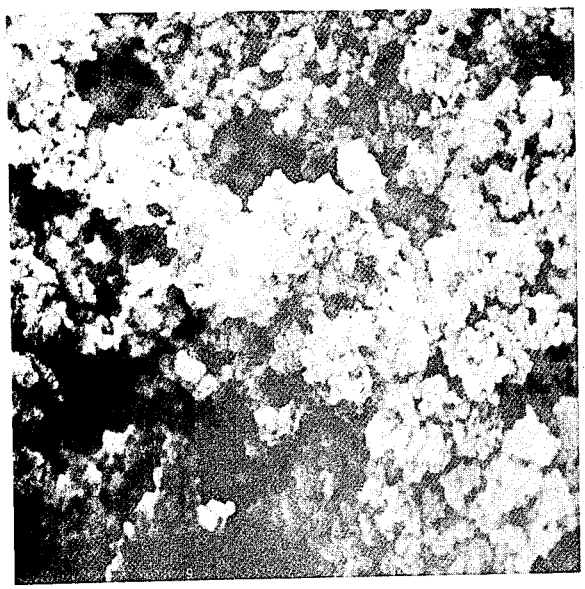
FIG. 5 is a photograph similar to that in FIG. 4 except that the reaction conditions were 0.4 equivalent weight and 35° C.
Figure 6:
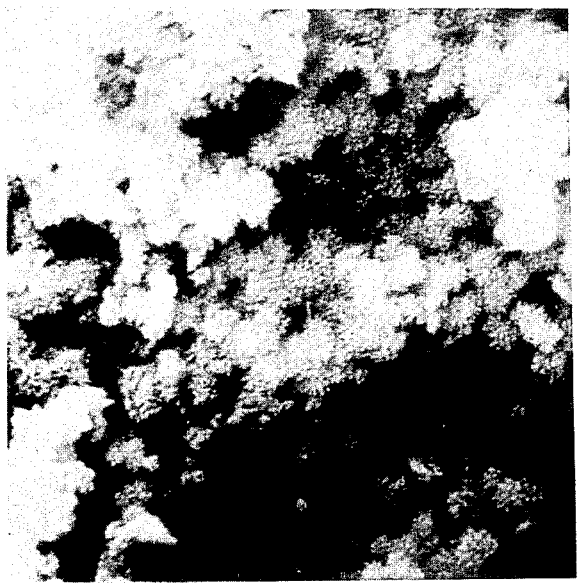
FIG. 6 is a photograph similar to that in FIG. 4 except that the reaction conditions were 0.4 equivalent weight and 40° C.
Figure 7:
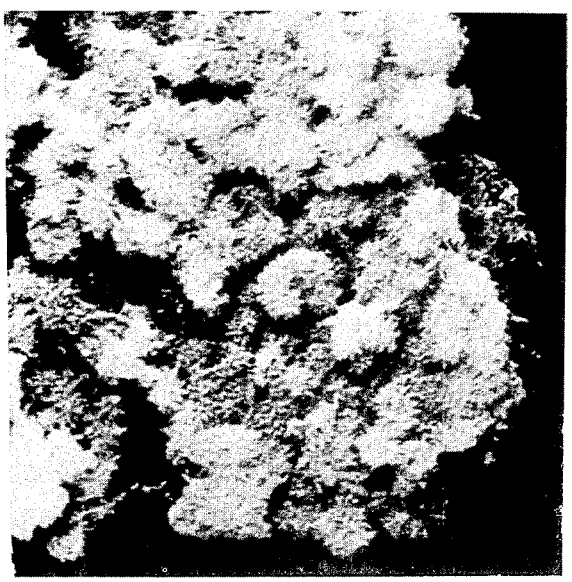
FIG. 7 is a photograph similar to that in FIG. 4 except that the reaction conditions were 0.4 equivalent weight and 45° to 55° C.
Figure 8:
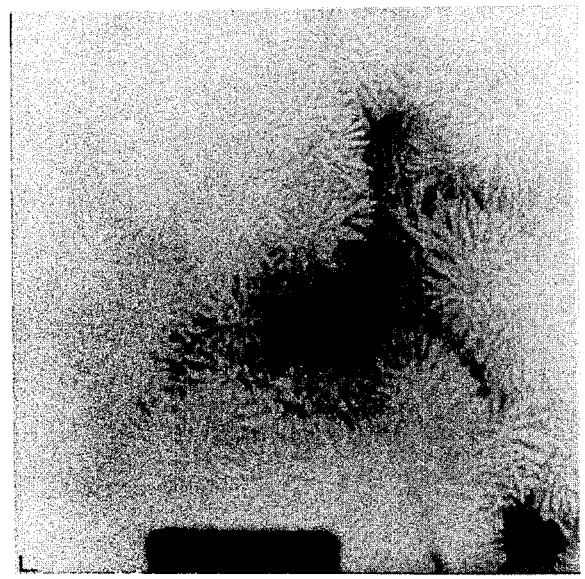
FIG. 8 is a photograph similar to that in FIG. 4 except that the reaction conditions were 0.3 equivalent weight and 55° to 66° C.
Figure 9:
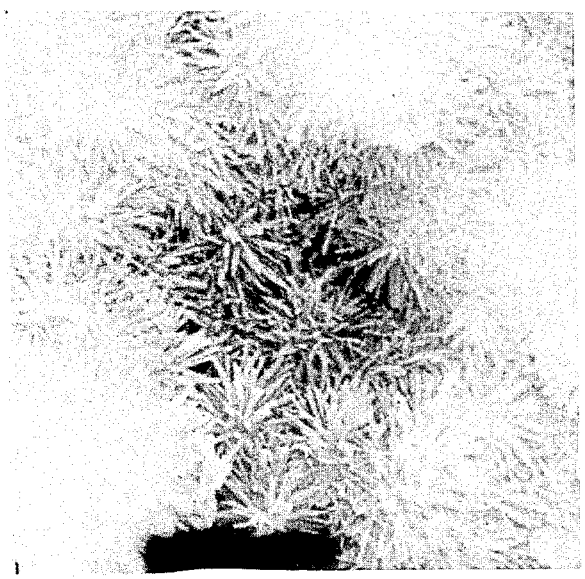
FIG. 9 is a photograph similar to that in FIG. 4 except that the reaction conditions were 0.3 equivalent weight and 65° C.

FIG. 2 represents an infrared absorptioon spectrum of the compound of this invention, with the horizontal axis graduated for wave number (cm⁻¹) and the vertical axis graduated for intensity of absorption. Table 2 indicates the results of FIG. 2 numerically in comparison with the data obtained for the conventional compounds $NaAlO(OH)HCO_3$ and $KAlO(OH)HCO_3$.

(Table 2)

The infrared absorption spectrum of MAlO(OH)HCO₃ (M: Alkali)

| | | NaAlO(OH)HCO₃ | | KAlO(OH)HCO₃ | | New Compound | |
|---|---|---|---|---|---|---|---|
| Assignment | | Wave No. (cm⁻¹) | strength | Wave No. (cm⁻¹) | strength | Wave No. (cm⁻¹) | strength |
| OH | stretching | 3280 | s | 3440 | s | 3400 | s |
| NH₄ | stretching | — | — | — | — | 3100 | s |
| CO₃ | stretching | 1550 | vs | 1540 | s | — | — |
| CO₃ | stretching | 1400 | vs | 1400 | s | 1390 | s |
| CO₃ | stretching | 1090 | m | 1100 | m | 1100 | m |
| OH | bending modes | 950 | s | 990 | s | 980 | s |
| CO₃ | bending modes | 858 | m | 866 | m | 858 | m |
| CO₃ | bending modes | 842 | m | 845 | w | — | — |
| CO₃ | bending modes | 727 | m | 760 | w | 760 | w |
| CO₃ | bending modes | 695 | ms | 745 | w | 740 | w |
| Al-O | | — | — | 660 | w | — | — |

Figure 3:
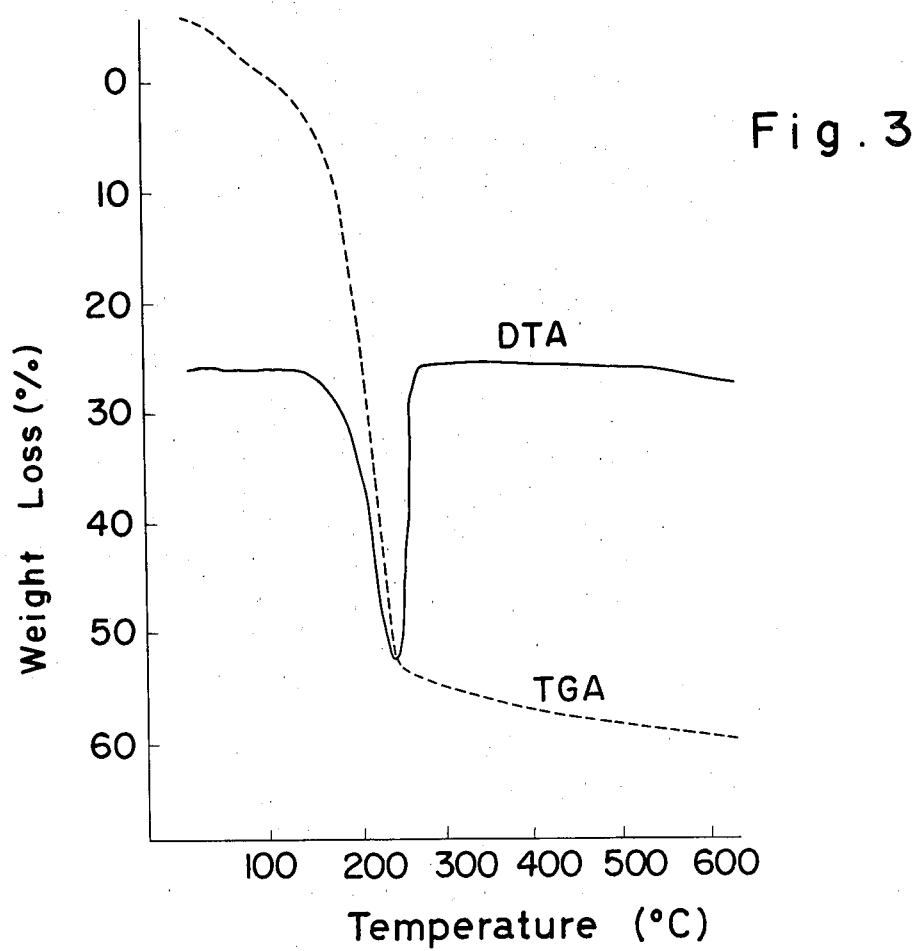
FIG. 3 is a graph showing the results of measurements made by differential thermal analysis and thermobalance of $NH_4AlCO_3(OH)_2$.

FIG. 3 is a graph showing the results of measurements of the compound of this invention by means of differential thermal analysis and thermobalance, with the continuous line indicating the results by differential thermal analysis and the dotted line those by thermobalance respectively. In the graph, the horizontal axis is graduated for temperature (°C) and the vertical axis is graduated for weight loss (%).

FIG. 4 through FIG. 9 scanning electron microscope photographs (1 × 10⁴ magnifications) of crystals formed at various reaction temperatures.

The reaction temperatures and equivalent weight of aluminum salt used in producing the crystals shown in FIGS. 4, 5, 6, 7, 8 and 9 are respectively 25° C, 0.4; 35° C, 0.4; 40° C, 0.4; 45° to 50° C, 0.4; 55° to 60° C, 0.3; and 65° C, 0.3.

It will be note from these photographs that the production of needle-like crystals becomes more pronounced with rising temperature.

$NH_4AlCO_3(OH)_2$ has a specific gravity of 1.97, a decomposition temperature of 223° C and a refractive index of 1.514 – 1.522, shows insolubility to water and solubility to acids and alkalis and abounds in filtrability because of its small bulk density and large void ratio. Thus, the properties of $NH_4AlCO_3(OH)_2$ are totally different from those of $NaAlCO_3(OH)_2$ and $KAlCO_3(OH)_2$ which both contain involatile alkali components.

Owing to the properties described above, $NH_4AlCO_3(OH)_2$ of the present invention is suitable for the various industrial uses which have been developed newly.

Upon thermal decomposition, $NH_4AlCO_3(OH)_2$ readily produces alumina. This alumina is useful as a commercial powdery raw material for the manufacture of sintered alumina of high purity, alumina of high purity for synthetic gems, catalysts, catalyt carriers, activated alumina, medicines and drugs, cosmetic articles, tooth powder and fillers for rubber products, plastic products, printing inks, paints and agricultural pesticides, etc.

Now, follows an explanation of the method by which the sintered alumina of high purity is manufactured by using $NH_4AlCO_3(OH)_2$ as the raw material. When $NH_4AlCO_3(OH)_2$ is used as the raw material, the sintered alumina can be manufactured at a temperature lower than when the manufacture is carried out by the conventional method. According to the conventional method, a sintered alumina of high purity is obtained, as described earlier, by burning at elevated temperatures aluminum hydroxide obtained generally by the Bayer process and thereby producing α-alumina, pulverizing the α-alumina for a long time, thereafter mixing the pulverized α-alumina with a crystal-growth regulating agent and a sintering accelerator and subsequently sintering the resultant mixture at temperatures around 1,900° C. In contrast, $NH_4AlCO_3(OH)_2$ of the present invention readily produces α-alumina in a powdery form when it is thermally decomposed. The α-alumina produced from such $NH_4AlCO_3(OH)_2$ as the raw material has an average particle diameter of not more than 0.5 μm and this product is sintered at temperatures below 1,700° C. This means that the desired sintering can be effected at a temperature about 200 Centigrade degrees lower than when the sintered α-alumina is manufactured for the α-alumina produced by the conventional Bayer process. In addition, $NH_4AlCO_3(OH)_2$ is obtained in a powdery form and, therefore, obviates necessity for any special treatment either for pulverization or for dealkalinization by way of preparation for thermal decomposition.

Now a typical procedure for producing crystals of $NH_4AlCO_3(OH)_2$ suitable for the manufacture of an alumina powder excelling in sintering property will be described. Ammonium hydrogen-carbonate and ammonium aluminum sulfate are allowed to react with each other by fixing the concentration of the former compound at 2M and that of the latter compound at 0.2M, the rate of dropwise introduction of the latter compound into the former compound at 0.8 liter per hour and the molar ratio of the former compound to the latter compound at 15, with only the reaction temperature varied. The results indicate that the crystals of $NH_4AlCO_3(OH)_2$ which are produced when the reaction temperature falls in the range of from 25° to 45° C form the raw material that gives α-alumina of the most desirable sintering property. The sintering property of the α-alumina is sharply degraded as the reaction temperature exceeds 45° C mainly because the product is affected in its crystallinity by temperature. If the reaction temperature is low, the reaction system entails formation of boehmite and consequently the product has its sintering property degraded. Temperatures below the range have less adverse effect upon the product's sintering property than those exceeding the range. Substantially, 25° C is the lower limit to the reaction temperature from the practical point of view. The temperature at which $NH_4AlCO_3(OH)_2$ is fired for the purpose of thermal decomposition has bearing upon the sintering property of the powdered alumina obtained consequently. The produced powdered alumina exhibits the most desirable sintering property when the firing is carried out at temperatures in the range of from 1,250° to 1,300° C. When the firing temperature fails to reach the lower limit 1,250° C of the range, the shrinkage due to firing tends to increase. When it exceeds the upper limit 1,300° C of the range, however, the particle diameter of the product tends to increase. In either case, the product's sintering property in inferior.

When the α-alumina obtained by the method of this invention is mixed with 5% of a organic binder such as, for example, Carbowax, molded under a pressure of 1 ton/cm² and then sintered in the air at 1,600° C for 60 minutes, the product's bulk density reaches more than 3.80 g/cc.

With the α-alumina of the Bayer process which has heretofore been used, it is difficult to obtain a product having a bulk density exceeding 3.00 g/cc, as indicated in the preferred embodiments, by carrying out the sintering at 1,600° C for 60 minutes even in the α-alumina is pulverized prior to the sintering. In order for this α-alumina to give a sintered product so compact as to show a bulk density over 3.80 g/cc, the sintering must be carried out at temperatures of not less than 1,800° C. If the alumina of the present invention is used in manufacturing a sintered product having an alumina content of about 85% by sintering a mixture consisting of 80% of alumina and 20% of such additives as crystal-growth regulating agent and sintering accelerator, the product obtained by carrying out the sintering at 1,350° C for 60 minutes will be so compact in texture as to show a bulk density of about 3.50. To obtain a sintered product having the same compactness by using the conventional alumina of the Bayer process, the sintering must be carried out at a higher temperature of about 1,500° C.

According to the method of this invention, the firing for the manufacture of a low-alumina sintered product can be carried out at a lower temperature as effectively as in the manufacture of the sintered alumina of high purity. Thus, the method of the present invention enjoys notable commercial advantages such as lower fuel cost, reduced cost of furnace material and enlarged scope of usable heat sources.

Now the present invention will be described with reference to preferred embodiments of the invention. This invention is not limited to these examples.

EXAMPLE 1

In a jacketed reactor can provided with an agitator, 15 liters of water and 2,370 g of ammonium hydrogencarbonate ($NH_4HCO_3$) were put together to produce a solution and, while the solution was kept under thorough agitation, an aluminum chloride solution separately prepared by having 1,205 g of aluminum chloride ($AlCl_3·6H_2O$) dissolved in 12.5 liters of water was added thereto at a rate of 0.04 liter/minute (equivalent to 2.4 liters/hour) so that the compounds were allowed to react at a temperature of 37° C with the equivalent weight ratio of $Al/NH_4$ fixed at 0.5. The reaction mixture was thereafter left to age at the same temperature for 20 minutes and then washed twice by means of decantation. The precipitate was separated by filtration and dried at 105°-110° C. Consequently there was obtained 665 g of a white fine powder. At the end of said reaction, the reaction mixture was found to have a pH value of 8.4. The analyses and the chemical composition of the product were as shown below. (wt %)

$Al_2O_3$ — 37.32%, $CO_2$ — 29.00%, $NH_4$ — 11.85%
$(NH_4)_{0.90}Al(CO_3)_{0.90}(OH)_{2.00}$

EXAMPLE 2

In a jacketed reactor can provided with an agitator, 20 liters of water and 3,160 g of ammonium hydrogencarbonate ($NH_4HCO_3$) were put together to produce a solution and, while the solution was kept under thorough agitation, an ammonium aluminum sulfate solution separately prepared by having 2.264 g of ammonium aluminum sulfate $[(NH_4)_2SO_4·Al_2(SO_4)_3·24H_2O]$ dissolved in 12.5 liters of water was gradually added thereto at a rate of 0.11 liter/minute so that the compounds were allowed to react at a temperature of 37° C with the equivalent weight ratio of $Al/NH_4$ fixed at 0.375. The reaction mixture was thereafter left to age at the same temperature for 15 minutes and then washed twice by means of decantation. The precipitate was separated by filtration and dired at 105°-110° C. Consequently, there was obtained 667 g of a white powder. At the end of the reaction, the pH value of the reaction mixture was 8.5. The analyses of the product and the rational formula based on said analyses were as shown below.

$Al_2O_3$ — 36.99%, $CO_2$ — 30.75%, $NH_4$ — 13.00%
$(NH_4)·Al(CO_3)_{0.96}(OH)_2$

FIG. 1 represents an X-ray diffraction diagram of $(NH_4)·Al(CO_3)_{0.96}(OH)_2$ obtained by the procedure of this example. In the diagram, the horizontal axis is graduated for diffractive angle 2θ and the vertical axis is graduated for intensity of diffraction ray.

EXAMPLE 3

Similarly to the procedure of Example 1, a 2M solution of ammonium hydrogencarbonate and a 0.2M solution of ammonium aluminum sulfate were allowed to react, with the equivalent weight ratio fixed at 0.4 (the molar ratio of ammonium aluminum sulfate/ammonium hydrogencarbonate = 1/15) and the reaction temperature and the rate of dropwise introduction varied as indicated in Table 3. The yield for each test run was determined by measuring, through chemical analysis, the $Al_2O_3$, $CO_2$ and $NH_4$ contents of the product obtained by drying at 105°–110° C and calculating the concentration (percentage) of $NH_4AlCO_3(OH)_2$ contained in the product. The results were as shown in Table 3. The precipitates obtained were invariably found to contain aluminum hydroxide besides $NH_4AlCO_3(OH)_2$.

(Table 3)

| Rate of dropwise introduction Reaction temperature | 0.1 liter/hour per 3 liters of mother liquid | 0.5 liter/hour per 3 liters of mother liquid | 1.0 liter/hour per 3 liters of mother liquid | 2.0 liter/hour per 3 liters of mother liquid |
| --- | --- | --- | --- | --- |
| 35° C | 95 | 94 | 95 | 77 |
| 50° C | 70 | 95 | 90 | 80 |
| 65° C | 45 | 84 | 90 | 85 |

The ease with which the reaction mixture was filtered and washed decreased with the decreasing yield of $NH_4AlCO_3(OH)_2$. This was because the decrease of yield was in proportion to the increasing by-production of aluminum hydroxide in a gel form.

As the rate of dropwise introduction was increased, there ensued local shortage of $HCO_3$ ions and consequent decline in the yield of $NH_4AlCO_3(OH)_2$. When the reaction was carried out at an increased temperature and a lowered rate of dropwise introduction, the $NH_4HCO_3$ component of the mother liquid decomposed to entail shortage of $HCO_3$ ions and change of pH value. Consequently, the atmosphere for the formation of $NH_4AlCO_3(OH)_2$ ceased to exist.

In the example described above, only reaction conditions which permit production of $NH_4AlCO_3(OH)_2$ of relatively high purity were indicated. The manufacture of $NH_4AlCO_3(OH)_2$ is not limited to the range embracing these reaction conditions.

EXAMPLE 4

By following the procedure of Example 1, a 0.2M solution of ammonium aluminum sulfate was added dropwise into a 2.0M solution of ammonium hydrogencarbonate at a rate of 0.3 –0.4 liter/hour per liter of the mother liquid, with the reaction temperature and the equivalent weight ratio of the aluminum salt solution to the mother liquid varied as indicated in Table 4. The yields obtained in terms of concentrations of $NH_4AlCO_3(OH)_2$ in the resultant reaction mixtures were as shown in Table 4. The yields were calculated in the same manner as described in Example 3.

(Table 4)

| Reaction temperature | Al/NH₄ Equivalent weight ratio | | | | | |
| --- | --- | --- | --- | --- | --- | --- |
| | 0.75 | 0.6 | 0.4 | 0.2 | 0.1 | 0.075 |
| 25° C | 55 | 80 | 88 | 88 | 90 | 90 |
| 35° C | 68 | 95 | 95 | 98 | 95 | 98 |
| 45° C | 70 | 95 | 98 | 99 | 98 | 99 |
| 55° C | 45 | 80 | 96 | 96 | 96 | 98 |
| 65° C | 30 | 55 | 70 | 85 | 95 | 95 |
| 70° C | 5 | 5 | 8 | 12 | 30 | 45 |

It is evident from the table that the yield of $NH_4AlCO_3(OH)_2$ increases with the increasing amount of ammonium hydrogen-carbonate based on that of aluminum. In consideration of the solubility of ammonium hydrogencarbonate in water, it is inferred that when the equivalent weight ratio is less than 0.075, the amount of the mother liquid is too large for the reaction to proceed smoothly. The ammonium hydrogencarbonate of the mother liquid is gradually decomposed in an aqueous solution and this decomposition is accelerated by an increase of temperature. The highest temperature at which the reaction could be effectively carried out was found to be 65° C. At temperatures below 25° C, the activity of $HCO_3$ ions was weakened and the purity of the product was consequently lowered.

EXAMPLE 5

Into 3 liters of a 2M solution of ammonium hydrogencarbonate, 2 liters of a 0.2M solution of ammonium aluminum sulfate was introduced dropwise under continued agitation at a rate of 0.8 liter per hour, with the liquid temperature maintained at 35° C to allow the compounds to react. The crystals of $NH_4AlCO_3(OH)_2$ consequently formed were separated by filtration, dried and thereafter burned at 1,280° C for 60 minutes to produce α-alumina.

This α-alumina was mixed with 5% of Carbowax added thereto and the resultant mixture was molded under a pressure of 1 ton/cm² and sintered at 1,600° C for 60 minutes. Consequently, there was obtained a sintered product having a bulk density of 3.83.

COMPARATIVE EXAMPLE

Four kinds of ceramic-grade alumina of the Bayer process available in the market were pulverized for 48 hours. When the resultant alumina powders were subjected to the treatment under entirely the same conditions as those of Example 5, the sintered products were found to have bulk densities ranging from 2.51 to 2.95, with the average at 2.74. Comparison shows that the 60 -alumina obtained by the present invention has a notably high sintering property.

EXAMPLE 6

By following the procedure of Example 5, a 2M solution of ammonium hydrogencarbonate and a 0.2M solution of ammonium aluminum sulfate were caused to react with each other, with the rate of dropwise introduction fixed at 0.8 liter/hour and the molar ratio of ammonium hydrogencarbonate/ammonium aluminum sulfate fixed at 15 and the reaction temperature varied to 25° C, 35° C, 45° C and 65° C. The crystals of $NH_4AlCO_3(OH)_2$ consequently obtained were treated after the manner of Example 5 and then subjected to firing at 1,600° C for 60 minutes. The bulk densities were as shown in Table 5.

(Table 5)

| Reaction temperature (° C) | Bulk density after firing (g/cm²) |
| --- | --- |
| 25 | 3.75 |
| 35 | 3.83 |
| 45 | 3.19 |
| 65 | 2.20 |

From these results, it can be seen that the sintering property of the α-alumina obtained is suddenly degraded as the reaction temperature exceeds 45° C.

EXAMPLE 7

The alumina of the present invention obtained by the procedure of Example 5 and a composite consisting of 80% of the commercially available alumina of the Bayer process, 10% of gairome clay, 5% of dolomite, 4.5% of talc and 0.5% of magnesia were separately wet mixed in a pot mill for 5 hours, then dried, molded under a pressure of 1 ton/cm² and burned for 1 hour at different temperatures indicated below. The results were as shown in Table 6.

(Table 6)

| Firing temperature | Bulk density | |
| --- | --- | --- |
| | Alumina of this invention | Alumina of Bayer process |
| 1300 | 3.13 | 2.28 |
| 1350 | 3.50 | 2.85 |
| 1400 | 3.50 | 3.25 |
| 1500 | 3.46 | 3.47 |

The values given under the heading of "Alumina of Bayer process" are averages of the values obtained of the four kinds of alumina available in the market.

From the results given above, it is evident that the method of the present invention permits sintered products so compact as to show a bulk density of 3.50 to be obtained at temperatures at least 150 Centigrade degrees lower than those required in the conventional method.

EXAMPLE 8

By following the procedure of Example 5, a 2M solution of ammonium hydrogencarbonate and a 0.2M solution of ammonium aluminum sulfate were caused to react, with the reaction temperature fixed at 35° C and the molar ratio of Ammonium hydrogencarbonate/ammonium aluminum sulfate fixed at 15 and the rate of dropwise introduction varied to 0.5, 1.0, 1.5 and 2.0 liters/hour. The crystals of $NH_4AlCO_3(OH)_2$ consequently obtained were treated after the manner of Example 5 and then fired at 1,600° C for 60 minutes. The bulk densities were as shown in Table 7.

(Table 7)

| Rate of dropwise introduction (liter/hour) | Bulk density (g/cm³) |
| --- | --- |
| 0.5 | 3.82 |
| 1.0 | 3.83 |
| 1.5 | 3.81 |
| 2.0 | 3.05 |

The results given above indicate that the sintering property of the α-alumina is rather degraded when the rate of dropwise introduction exceeds 2 liters/hour.

What is claimed is:

1. A method for the manufacture at low temperatures, of a compactly sintered high-purity alumina having a bulk density greater than 3.8 g/cc, which comprises:
    adding to a solution of ammonium hydrogen carbonate having a concentration of from 40 g/l. to 270 g/l. a solution of at least one aluminum salt selected from the group consisting of aluminum chloride, aluminum nitrate, aluminum sulfate, ammonium aluminum sulfate and basic salts thereof having a concentration of from 5 g/l. to 150g/l. computed as aluminum oxide, the amount added being not less than 0.07 and not more than 0.75 of the equivalent weight computed as $Al/NH_4$, the rate of addition of said solution being from 0.03 l./hr. to 1.8 l/hr. per 1000 cc of said solution of ammonium hydrogen carbonate and the resulting addition reaction being conducted at a temperature of from 30° to 35° C and a pH of from 7.5 to 9.0,
    allowing the resultant solution to stand to permit growth of crystals of ammonium aluminum carbonate hydroxide,
    filtering said solution containing grown crystals of ammonium aluminum carbonate hydroxide to obtain crystals of ammonium aluminum carbonate hydroxide,
    drying the crystals,
    subjecting the dried crystals of ammonium aluminum carbonate hydroxide to thermal decomposition at temperatures in the range of from 1,250° to 1,300° C to afford α-alumina capable of being readily sintered,
    adding to said α-alumina an organic binder,
    molding the resultant mixture under pressure and
    sintering the molded mixture at temperatures in the range of from 1600° to 1700° C to obtain a compactly sintered high-purity alumina having a bulk density greater than 3.8 g/cc.

2. The method of claim 1, wheren said α-alumina has an average particle diameter of about 0.5μm.

* * * * *